United States Patent [19]

Massey

[11] Patent Number: 5,057,420

[45] Date of Patent: Oct. 15, 1991

[54] BOVINE NUCLEAR TRANSPLANTATION

[75] Inventor: Joseph M. Massey, College Station, Tex.

[73] Assignee: Granada Biosciences, Inc., Houston, Tex.

[21] Appl. No.: 599,256

[22] Filed: Oct. 16, 1990

Related U.S. Application Data

[63] Continuation of Ser. No. 58,904, Jun. 5, 1987, abandoned.

[51] Int. Cl.$^5$ .............................................. C12N 15/00
[52] U.S. Cl. ............................. 435/172.2; 435/172.3; 800/2; 800/DIG. 6; 935/53; 935/111
[58] Field of Search ............... 435/172.2, 172.3, 240.1, 435/240.26; 800/2, DIG. 6; 935/53, 111

[56] References Cited

U.S. PATENT DOCUMENTS 4,664,097  5/1987  McGrath et al. .................... 128/1 R

FOREIGN PATENT DOCUMENTS 2199845  7/1988  United Kingdom .

OTHER PUBLICATIONS

McGrath et al., Science 220:1300-1302 (1983).
Lohse et al., Theriogenology 23(1):205 (1985).
Loskutoff et al., Theriogenology 25(1):168 (1986).
"Nuclear Transplantation in the Bovine Embryo: Assessment of Donor Nuclei and Recipient Oocyte", R. S. Prather et al, Biology of Reproduction, vol. 37, 859-866 (1987).
Transplantation of Living Nuclei from Blastula Cells into Enucleated Frogs Eggs, R. Briggs and T. J. King, Proceedings of the National Academy of Sciences, vol. 38, pp. 455-463 (1952).
Adult Frogs Derived from the Nuclei of Single Somatic Cells, J. B. Gurdon, Developmental Biology, vol. 4, pp. 256-273 (1962).
Development and Chromosomal Constitution of Nuclear-Transplants Derived from Male Germ Cells, M. A. DiBerardino and N. J. Hoffner, Journal of Experimental Zoology, vol. 176, pp. 61-72 (1971).
Activation of Dormant Genes in Specialized Cells, M. A. DiBerardino, N. J. Hoffner and L. D. Etkin, Science, vol. 224, pp. 946-952 (Jun. 1984).
Methods and Success of Nuclear Transplantation in Mammals, A. McClaren, Nature, vol. 309, pp. 671-672, (Jun. 21, 1984).
Nuclear Transplantation in Mouse Embryos, J. McGrath and D. Solter, The Journal of Experimental Zoology, vol. 228, pp. 355-362 (1983).
Development of Reconstituted Mouse Eggs Suggests Imprinting of the Genome During Gametogensis, M. A. H. Surani, S. C. Barton, M. L. Norris, Nature, vol. 308, pp. 548-550 (Apr. 5, 1984).
Full-Term Development after Transplantation of Parthenogenetic Embryonic Nuclei into Fertilized Mouse Eggs, P. C. Hoppe, K. Illmensee, Proceedings of the National Academy of Sciences, vol. 79, pp. 1912-1916 (Mar. 1982).
Nuclear Transplantation in Mus musculus: Developmental Potential of Nuclei from Preimplantation Embryos, K. Illmensee, P. C. Hoppe, Cell, vol. 23, pp. 9-18 (Jan. 1981).
Electric Field-Induced Cell-to-Cell Fusion, U. Zimmerman and J. Vienken, Journal of Membrane Biology, vol. 67, pp. 165-182 (1982).
Multiplication of Bovine Embryos, R. S. Prather, F. L. Barnes, J. M. Robl and N. L. First, Society for the Study of Reproduction, Ithaca, New York (1986) Biology of Reproduction, vol. 34, Supplement 1, p. 192, Jun. 4, 1986.
Nuclear Transplantation in Bovine Embryos, J. M. Robl, R. Prather, W. Eyestone, F. Barnes, D. Northey, B. Billigan and N. F. First, Theriogenology, vol. 25, No. 1, p. 189 (Jan. 1986).
Nuclear Activation and Transplantation in the Rabbit Oocyte, S. L. Stice, H. M. Bean, J. M. Robl, Biology of Reproduction, Supplement 1, p. 77 (1987); presented Society for the Study of Reproduction; 20th Anniversary Meeting, Urbana, Illinois (Jul. 1987).
Electrofusion for the Pronuclear Transplantation of Mouse Eggs, Y. Tsunoda, Y. Kato and Y. Schioda, Gamete Research, vol. 27, No. 1, p. 209 (Jan. 1987).
Multiplication of Bovine Embryos, F. L. Barnes, R. S. Prather, J. M. Robl and N. L. First, Theriogenology, vol. 27, No. 1, p. 209, Jan. 1987.
Nuclear Transplantation in Bovine Embryos, J. M. Robl, R. Prather, E. Barnes, W. Eyestone, D. Northey, B. Gilligan and N. L. First, Journal of Animal Science, vol. 64, pp. 642-647 (1987).
Nuclear Transplantation in Mouse Embryos: Assessment of Nuclear Function, F. L. Barnes, J. M. Robl and N. L. First, Biology of Reproduction, vol. 36, pp. 1267-1274 (1987).
Nuclear Transplantation in Sheep Embryos, S. M. Willadsen, Nature, vol. 320, No. 6057, pp. 63-65, Mar. 6, 1986.

Primary Examiner—Elizabeth C. Weimar
Assistant Examiner—Jasemine C. Chambers
Attorney, Agent, or Firm—Margaret A. Boulware

[57] ABSTRACT

A process to produce viable bovine embryos through nuclear transplantation. The process utilizes nuclear material from 4 cell and later stage developed embryos recovered from inseminated donor cows through nonsurgical or surgical means. Recipient eggs or oocytes are recovered and a portion of the ooplasm removed by micromanipulation. Individually separated cells from the nuclear material donor embryo are inserted into the recipient oocyte. The oocyte fragment and nuclear donor material are electrofused. The embryo is cultured in vitro, transferred for an interim time to a sheep oviduct and then transferred to a cow for gestation.

20 Claims, No Drawings

BOVINE NUCLEAR TRANSPLANTATION

This application is a continuation of co-pending application Ser. No. 058,904, filed June 5, 1987, now abandoned.

BACKGROUND OF THE INVENTION

Nuclear transfer involves the transplantation of living nuclei from typically embryonic cells to unfertilized eggs. The early research on vertebrates was performed in amphibians. The embryonic frog blastomere cells were separated and the nuclear material was introduced into frogs' eggs which had been enucleated. See Transplantation of Living Nuclei From Blastula Cells into Enucleated Frogs Eggs, R. Briggs and T. J. King, *Proceedings of the National Academy of Sciences*, Volume 38, pages 455–463, 1952. Further experimentation was performed on amphibians and amphibian eggs to determine if nuclear material from adult frog somatic or germinal cells could be transplanted to eggs and develop into a normal larva. Development and Chromosomal Constitution of Nuclear-Transplants Derived from Male Germ Cells, M. A. Berardino and N. Hoffner, *Journal of Experimental Zoology*, Volume 176, pages 61–72, 1971. There is a great degree of uncertainty as to when the genetic material of a cell can no longer be reprogrammed, which limits the stage of development of donor nuclear material.

Transplantation of nuclear material in mammals has proved very difficult to achieve which is in part due to the microsurgical techniques on mammalian embryos and eggs. The microsurgical techniques can be destructive to delicate cell structure which damages the cell material used in the later stage of the transplantation procedure. An alternative procedure is to deliver the nuclear material to a recipient egg by fusion of an intact cell or a karyoplast consisting of a nucleus surrounded by a piece of plasma membrane to the egg. The manipulation to isolate a karyoplast is performed in the presence of cytochalasin B. Methods and Success of Nuclear Transplantation in Mammals, A. McLaren *Nature*, Volume 109, June 21, 1984. Also, once the nuclear material has been transplanted to a recipient a mammalian egg there is fusion of the cellular material to produce a new viable embryo. The fusion can be aided or induced with virus or electro-field induced. However, the conditions for fusion are not predictable. Electric Field-Induced Cell-to-Cell Fusion, U. Zimmermann and J. Vienke, *Journal of Membrane Biology*, Volume 67, page 165–182 (1982).

Nuclear transplantation in higher mammals has been attempted. Successful nuclear transplantation and cell fusion was achieved for sheep embryos when individual blastomeres from 8 and 16 cell embryos were used as the nuclear donors into enucleated or nucleated halves of unfertilized eggs. Nuclear Transplantation in Sheep Embryos, S. M. Willadsen, *Nature*, Volume 320, pages 63–65, March 1986. Nuclear transplantation has been attempted in bovine embryos, however, the embryos developed only 43 days out of a nine month typical gestation period. Nuclear Transplantation in Bovine, J. M. Robl, R. Prather, W. Eyestone, F. Barnes, D. Northey, B. Gilligan, and N. L. First, *Theriogenology*, Volume 25, No. 1, January 1986. Successful nuclear transplantation and embryo development in higher mammals has great implications in breeding.

SUMMARY OF THE INVENTION

Selective cattle breeding involves the selection of the desired bull as the sperm donor and the desired female for the egg donor. Typically the female was artificially inseminated with the bull semen in a selective breeding program. The female may be superovulated to produce several eggs and therefor several embryos. The embryos may then be transferred to recipient cows for gestation.

This invention is a method for producing a relatively large number of identical bovine embryos that can be transferred to surrogate female cows for gestation. The process involves the separation of a donor embryo into single cells which were transplanted into nucleated or enucleated oocytes for further development. The donor embryo can be from a 4 to at least a compacted morula stage embryo (approximately 64 cells). The earlier stage embryos must be removed surgically. However, the 16 cell to compacted morula cell stage embryos can be removed nonsurgically which is a much more economical method. For commercial breeding application the embryos used as nuclear donors are selected from cows that have been inseminated with the selected bull semen to produce the desired cross or an embryo developed from a prior nuclear transfer. However, this process may be used with any bovine multicellular embryo. Also, good results have been obtained with previously deep frozen embryos.

The stage of the donor embryo at the 16 cell to compacted morula stage of development makes the process attractive from an economical standpoint because of the increased number of donor nuclear cells as well as the lack of surgical technique necessary to remove the embryo initially. The process, whether or not a surgical procedure is used to remove embryos, enables one to prepare embryo clones with a good success rate in viability. Although there were some losses in viability of the embryos during the early stage of development, this process will produce multiple calves with identical genetic makeup.

Also, embryos that were developed through this procedure have in turn been used as nuclear donor cells for subsequent recipient eggs. This produces viable cattle embryos by transplantation of nuclear material from embryos which are themselves the products of nuclear transplantation.

DESCRIPTION OF THE PREFERRED METHOD

The process constitutes several steps which generally includes isolating the recipient oocytes from the donor cows, recovering embryos from donor cows, transferring the nuclear material from the embryo to the recipient oocytes, fusing the oocyte fragment and the donor cells to form an embryo, and culturing the embryo before transferring into a recipient cow for gestation. The recipient oocytes are collected from cows which have been induced to ovulate at a predicted time with prostaglandin $F_2$ alpha (pgF$_2\alpha$). Human chorionic gonadotropin (hCG) can also be administered to further predict the ovulation time. The oocytes were collected approximately 39 hours after hCG or 87 hours after pgF$_2\alpha$ administration. Approximately 4,000 I.U. of hCG were administered. If desired, the cow can be superovulated to produce multiple eggs by administering FSH hormone. The oocytes were collected surgically approximately 39 hours after hCG administration. This is approximately 10 to 14 hours after ovulation.

The zona pellucida of the egg was cleaned of all cells and debris with a cleaning pipette. The eggs were placed in a solution of Dulbecco's Phosphate Buffed Saline (PBS). After cleaning the eggs were placed on a micromanipulation stage. Using a fine glass needle, a slit was made in the zona pellucida directly over the polar body traversing the perivitelline space such that the zona pellucida is opened slightly more than 180° along its equator with the polar body near the middle of the slit. If the polar body was not located, a slit of the same dimension was made in the part of the zona pellucida which spans the widest portion of the perivitelline space.

After the recipient oocytes have been slit, they were placed in PBS containing Cytochalasin B (5 micrograms per/ml; Sigma) for at least half an hour before further processing.

The nucleus donor embryo is typically collected from a cow which has been artificially inseminated, however this procedure may be used with any cow embryo from the 4 cell to compacted morula stage of development. For embryo donors from the 16 cell to compacted morula stage, nonsurgical procedures are used to flush the embryo from the cow uterus. The donor embryos are collected after four and half to six days after behavioral estrus is observed. The embryos are examined after collection to determine the stage of development. In some cases the embryo nuclear donor was from deep frozen embryos. Typically 16 to 32 cell embryos are collected on day five. Also late morulae and early blastocysts collected on day six have been used.

The zona pellucida of the nucleus donor embryo was slit with a fine glass needle $\frac{3}{4}$ or more around the equator. The embryo was coaxed out of the zona pellucida with the tip of the needle and transferred to a petri dish with fresh PBS solution. The embryo was separated into blastomere cells by repeated suction in a micropipette. An alternative procedure is to remove the individual cells from the embryo by drawing the cells one at a time into a micropipette with an inner diameter approximately the same size as the cells.

Returning to the oocytes which have been previously slit, if the polar body was clearly visible, the polar body and an adjacent part of the ooplasm corresponding to between $\frac{1}{4}$ and $\frac{1}{3}$ of the total volume of the cell was sucked into a micropipette. In oocytes with no visible polar body, about $\frac{1}{3}$ of the ooplasm was removed by suction with a micropipette. The ooplasm which was removed can be inserted into an evacuated zona pellucida. The foreign zona pellucida can be obtained from an egg that is not chosen as a recipient oocyte. Thus, one egg can yield two recipient oocytes if a foreign zona pellucida is used.

An alternative procedure in preparing the egg utilizes a micropipette to pierce the zona pellucida. A micropipette was inserted in the egg and about half of ooplasm was aspirated. The zona pellucida encloses the remaining ooplasm of the donor egg and the ooplasm removed with the micropipette was placed in a recipient zona pellucida.

The enucleated half of the egg, the half without the polar body, is presumed to fuse with the nuclear material that comes from the separated embryo cells. However, sometimes it is not possible to identify the polar body so it was difficult to determine where the nuclear material lies. It has been postulated that an egg with nuclear material should not be viable with additional nuclear material from the embryo cell. There is sometimes more than a 50% survival rate when one egg is divided and nuclear material transplanted into both halves. This supports the premise that possibly the nuclear material was broken up to a degree that it is not viable. However, other theories could support the simultaneous viable development of both egg halves.

The disassociated blastomeres of the donor embryo were transferred to the halved recipient oocytes. A blastomere was transferred to the perivitelline space and brought in close contact with the oocyte fragment. The blastomere/oocyte fragments were then ready for fusion. The preferred method of fusion is electrofusion.

The embryos were placed in PBS at room temperature for one hour before electrofusion. The zonae pellucidae containing blastomere and egg halves were transferred to a petri dish containing fusion medium of 0.3M Mannitol, 0.1 mM $MgSO_4$, 0.05 mM $CaCl_2$ in distilled water or Zimmerman cell fusion media for approximately 25-30 minutes.

The blastomere/oocytes were transferred in the fusion medium to the chamber of an electrofusion apparatus (Zimmermann; GCA, Chicago). With the Zimmerman electrofusion apparatus the two electrical poles are wires which are parallel to each other in the center of the plate. The oocyte with the blastomere are lined up at right angles to either wire such that the oocyte touches the wire and the blastomere portion is opposite to the wire. The blastomere/oocytes are exposed to the following fusion conditions; cell alignment (600 kHz, 6 V for 10 seconds), followed by 3 fusion pulses of 15 V with a pulse duration of 50.0 microseconds at 0.1 second interval. After the fusion pulses, the alignment voltage was reduced over one minute from 6 V to 0 V. All embryos were transferred to PBS and incubated at 37° C. for one hour. The embryos are then examined to determine in which fusion had occurred or is in progress.

A semi-solid medium such as agar can be used to embed the embryos prior to transfer to sheep oviducts. Several embryos can be embedded in one section of agar. The agar chip allows for normal development to occur in the ewe's oviduct even though the zonae pellucidae are not intact.

An agar solution was prepared with 0.6 g agar dissolved in 60 ml of 0.9% NaCl in distilled water by boiling. The agar solution was set aside to cool. The embryos were transferred to a PBS solution with 20% sheep or calf serum. When the agar solution has cooled to 30° to 35° C. the embryos are picked up in a small amount of PBS medium with a micropipette. Five to 10 ml of agar solution was poured into an empty petri dish and the embryos are transferred into the agar using the pipette. The agar containing the embryo was then placed in a petri dish containing PBS. The embryo in the agar is expelled from the pipette shaped as a small cylinder which is cut short as possible.

A second embedding takes place using a 0.6 gm agar dissolved in 50 ml of 0.9% NaCl in distilled water by boiling. The agar solution was cooled to 30° to 35° C. The first embedded embryos were completely covered. The second embedding with agar formed a chip not longer than 2.5 to 3 mm.

The agar embedded embryos were transferred into ligated oviducts of ewe for culture. Four to six days later the oviduct ewe was flushed with PBS solution which is inspected for the chip with the embedded embryo. The chip was cut open so that the cavity around the embryo is open and the embryo is dislodged with glass needles. After release from the agar chip the embryos were placed in fresh PBS at room temperature until they can be transferred to recipient cows in a conventional way.

The nucleus donor embryo used in this procedure can be a embryo which was produced from the nuclear transplantation procedure of this invention. This serial use of the nuclear material involves the use of nucleus donor embryo prepared following the steps of the above described procedure. The embryo recovered from the sheep is at a stage of development which can be used as a nucleus donor. The embryo cells are separated and fused with recipient oocytes as described above. The use of nuclear donor embryos prepared by nuclear transplantation can be performed serially such that nuclear material can be from several generations of embryonic material prepared by the procedures described herein.

The embryos recovered from the sheep may be deep frozen. At a later time the embryos are thawed and used in the procedure as described herein.

The following Tables I and II give the results of the nuclear transplantation of bovine embryo cells to oocytes as described by this procedure. Table I is a summary of first generation transfers in which the embryo used as the nucleus donor was from an artificially inseminated cow. Table II is a summary of second generation transfer in which the embryo used as the nucleus donor was from a first generation embryo developed by the nuclear transplantation process.

were born from the process of this invention demonstrating the success of the methods described.

Table II shows the use of second generation embryos, those developed by this invention, in subsequent nuclear transplantation. The embryos recovered from the sheep are used as nuclear material donors. Consequently, a descending number of generations can be cloned using the same genetic material using the steps of this transplantation process.

What is claimed is:

1. A process to produce viable bovine embryos through nuclear transplantation comprising the following steps:
   (a) collecting recipient oocytes from donor cows;
   (b) collecting embryos greater than 32 cells;
   (c) removing a portion of the ooplasm from the recipient oocyte;
   (d) separating the embryo cells into single donor cells for nuclear transplantation;
   (e) inserting said donor cell into the recipient oocyte;
   (f) electrofusing the oocyte and donor cell to form an embryo; and
   (g) culturing said embryo.

2. A process to produce viable bovine embryos of claim 1 wherein the embryos collected in step (b) are deep frozen and thawed for use later in the process described in claim 1.

3. A process to produce viable bovine embryos of claim 1 wherein in step (c) the portion of the ooplasm removed is corresponding to at least ⅓ of the total vol-

TABLE I

| | | BOVINE NUCLEAR TRANSPLANTATION 1ST GENERATION (GGI) | | | | | | | | |
|---|---|---|---|---|---|---|---|---|---|---|
| Embryo Stage | No. Donor Embryos | No. Attempted Fusion | No. Fusion Successful | No. Trans. Sheep | No. Recovered | Viable Embryos | No. Trans. Cow | No. Pregnant | Abortions | No. Live Calves |
| 16–20 cell | 8 | 115 | 98 | 101 | 81 | 29 | 23 | 12 | 4 | 8 |
| 21–32 cell | 14 | 326 | 261 | 290 | 256 | 71 | 63 | 14[1] | 2 | 4 |
| >32 cell | 6 | 145 | 121 | 125 | 107 | 26 | 25 | 4[2] | 1 | 0 |
| TOTAL | 28 | 586 | 480 | 516 | 444 | 126 | 111 | 30 | 7 | 12 |

[1]Fourteen transfers are pending pregnancy examination
[2]Four transfers are pending pregnancy examination

TABLE II

| | | BOVINE NUCLEAR TRANSPLANTATION SECOND GENERATION | | | | | | | | |
|---|---|---|---|---|---|---|---|---|---|---|
| Embryo Stage | No. Donor Embryos | No. Attempted Fusion | No. Fusion Successful | No. Trans. Sheep | No. Recovered | Viable Embryos | No. Trans. Cow | No. Pregnant | Abortions | No. Live Calves |
| >32 cell | 4 | 83 | 58 | 55 | 51 | 31 | 22 | 3 | 2 | 1 |

As shown in Table I, 16 cell stage embryos and higher were used. The highest cell stage tested was compacted morula of about 64 cells. The lower cell stage embryo nucleus donors were traditionally thought to be more suitable for transfer of nuclear material. However, Table I shows a good fusion and viability rate of the higher cell stage embryo compared to the lower cell stage.

The number of successful fusions are noted on both Table I and Table II. This figure was calculated based on visual observation of the embryos under a microscope after electrofusion. The number of successful fusions was rated by visual observation. Some of the embryos which did not pass the visual test for fusion were nevertheless transferred to the sheep for further culture.

Not all the embryos were carried through all the stages of the process as shown in the Tables. Live calves ume of the cell and is adjacent to and includes the polar body.

4. A process to produce viable bovine embryos of claim 1 wherein in step (c) about half of the ooplasm is removed comprises the additional steps;
   preparing a foreign zona pellucida to receive said ooplasm;
   inserting said removed ooplasm into said foreign zone pellucida; and
   following steps (d) through (e) of claim 1 utilizing the recipient oocyte and the zona pellucida with transferred ooplasm as a recipient oocyte.

5. A process to produce viable bovine embryos of claim 1 including the step of transferring the cultured embryo to a recipient cow for gestation.

6. A process to produce viable bovine embryos of claim 1 including the steps of transferring the electrofused embryo to a surrogate animal for culturing and subsequent transfer to a recipient cow for gestation.

7. A process to produce viable bovine embryos of claim 1 including the step wherein the electrofused embryo is embedded in a semi-solid medium; and transferring the embedded embryo into a surrogate animal for culturing.

8. A process to produce viable bovine embryos of claim 1 wherein said recipient oocytes are collected approximately 10 to 14 hours post ovulation from the donor cows.

9. A process to produce viable bovine embryos of claim 1 wherein said nuclear donor embryos are at least 33 cells.

10. A process to produce viable bovine embryos of claim 1 wherein said recipient oocytes are collected approximately 39 hours after hCG administration.

11. A process to produce viable bovine embryos of claim 1 wherein said recipient oocytes are collected approximately 87 hours after pgF$_2\alpha$ administration.

12. A process to produce viable bovine embryos through nuclear transplantation comprising the following steps:

(a) collecting oocytes from donor cows;

(b) collecting embryos greater than 32 cells;

(c) slitting the zona pellucida of at least one oocyte more than 180°;

(d) removing the polar body and at least ⅛ of the ooplasm of the oocyte;

(e) separating the embryo cells into disassociated blastomeres;

(f) inserting said blastomeres into the perivitelline space in close contact with the remaining ooplasm of the oocyte fragment;

(g) electro fusing the oocyte fragment and the blastomere to form an embryo; and (h) culturing said embryo.

13. A process to produce viable bovine embryos of claim 12 including the step of transferring the cultured embryo to a recipient cow for gestation.

14. A process to produce viable bovine embryos of claim 12 including the steps of transferring the electrofused embryo to a surrogate animal for culturing and subsequent transfer to a recipient cow for gestation.

15. A process to produce viable bovine embryos of claim 12 including the step wherein the electrofused embryo is embedded in a semi-solid medium; and transferring the embedded embryo into a surrogate animal for culturing.

16. A process to produce viable bovine embryos of claim 12 wherein said recipient oocytes are collected approximately 10 to 14 hours post ovulation from the donor cows.

17. A process to produce viable bovine embryos of claim 12 wherein said nuclear donor embryos are at least 33 cells.

18. A process to produce viable bovine embryos of claim 12 wherein said embryos used for donor cells have been deep frozen and subsequently thawed prior to step (d).

19. A process to produce viable bovine embryos of claim 12 wherein said recipient oocytes are collected approximately 39 hours after hCG administration.

20. A process to produce viable bovine embryos of claim 12 wherein said recipient oocytes are collected approximately 87 hours after pgF$_2\alpha$ administration.

* * * * *